(12) United States Patent
Mrowka et al.

(10) Patent No.: US 9,737,759 B2
(45) Date of Patent: *Aug. 22, 2017

(54) AUTOMATIC APPLICATION-BASED EXERCISE TRACKING SYSTEM AND METHOD

(71) Applicant: Genesant Technologies, Inc., Vienna, VA (US)

(72) Inventors: James J. Mrowka, San Mateo, CA (US); Paola N. Robey, Falls Church, VA (US); Daniel S. Robey, Falls Church, VA (US); Joseph A. Croswell, McLean, VA (US); Athanasios G. Christ, Reston, VA (US)

(73) Assignee: Genesant Technologies, Inc., Vienna, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/161,588

(22) Filed: May 23, 2016

(65) Prior Publication Data

US 2017/0014682 A1    Jan. 19, 2017

Related U.S. Application Data

(63) Continuation-in-part of application No. 15/041,780, filed on Feb. 11, 2016, now Pat. No. 9,449,530.

(60) Provisional application No. 62/193,879, filed on Jul. 17, 2015.

(51) Int. Cl.
  G06F 17/27    (2006.01)
  A63B 24/00    (2006.01)
  G06F 19/00    (2011.01)

(52) U.S. Cl.
  CPC ...... A63B 24/0062 (2013.01); G06F 17/2705 (2013.01); G06F 17/2765 (2013.01); G06F 19/3475 (2013.01)

(58) Field of Classification Search
  CPC ...... G06F 17/27; G06F 17/20; G06F 17/2705; G06F 17/271; G06F 17/2715; G06F 17/272; G06F 17/2725; G06F 17/273; G06F 17/2735; G06F 17/274; G06F 17/2745; G06F 17/275; G06F 17/2755; G06F 17/276; G06F 17/2765; G06F 17/2795; G06F 19/00; G06F 19/3431; G06F 19/3475; G06F 17/30
  USPC .................................................. 704/1, 9, 10
  See application file for complete search history.

(56) References Cited

U.S. PATENT DOCUMENTS

| | | | |
|---|---|---|---|
| 5,890,997 A * | 4/1999 | Roth | A63B 71/06 482/8 |
| 6,556,963 B1 | 4/2003 | Tetzlaff | |
| 7,076,438 B1 * | 7/2006 | Tobelmann | G06F 19/3475 128/921 |

(Continued)

Primary Examiner — Lamont Spooner
(74) Attorney, Agent, or Firm — Barry N. Young

(57) ABSTRACT

An automatic application-based exercise tracking system and methods comprising: i) voice-transcribed or typed text natural language processing and automatic tracking to record exercises, comprehensive exercise quantities, and calories burned data, and ii) multi-exercise administration to record multiple exercises and related data in a single user voice-transcribed or typed text submission. Further, such automatic application-based exercise tracking system is usable through computers, tablets, mobile phones, smart watches, wearables and other similar devices.

20 Claims, 11 Drawing Sheets

(56) References Cited

U.S. PATENT DOCUMENTS

| | | | |
|---|---|---|---|
| 8,690,578 B1* | 4/2014 | Nusbaum | G09B 19/00 128/905 |
| 8,924,239 B1* | 12/2014 | Kurple | G06F 19/3475 705/2 |
| 2002/0049736 A1* | 4/2002 | Chow | G06Q 30/06 |
| 2002/0124017 A1* | 9/2002 | Mault | A61B 5/222 600/300 |
| 2002/0156351 A1* | 10/2002 | Sagel | A23L 1/293 600/300 |
| 2004/0138820 A1* | 7/2004 | Morris | G06F 19/3475 702/19 |
| 2004/0229195 A1* | 11/2004 | Marggraff | G06K 7/10881 434/169 |
| 2005/0010416 A1* | 1/2005 | Anderson | G06F 17/27 704/271 |
| 2005/0113650 A1* | 5/2005 | Pacione | A61B 5/411 600/300 |
| 2005/0121504 A1* | 6/2005 | Sanders | G06F 19/3406 235/87 A |
| 2006/0293617 A1* | 12/2006 | Einav | A61H 1/0274 601/33 |
| 2007/0260483 A1* | 11/2007 | Nurmela | A61B 5/0022 705/2 |
| 2008/0077489 A1* | 3/2008 | Gilley | G06Q 30/02 705/14.11 |
| 2008/0162352 A1* | 7/2008 | Gizewski | G06F 19/345 705/50 |
| 2008/0306347 A1* | 12/2008 | Deutsch | G06F 19/3418 600/300 |
| 2009/0099873 A1* | 4/2009 | Kurple | G06Q 50/24 705/3 |
| 2009/0216629 A1* | 8/2009 | James | G06F 19/3418 705/14.19 |
| 2009/0219159 A1* | 9/2009 | Morgenstern | A63B 24/00 340/573.1 |
| 2011/0061027 A1* | 3/2011 | Brown | G06F 17/30731 715/840 |
| 2011/0153744 A1* | 6/2011 | Brown | G06F 17/30731 709/204 |
| 2012/0110458 A1* | 5/2012 | Brown | G06F 17/30575 715/733 |
| 2012/0303638 A1* | 11/2012 | Bousamra | G06F 19/3475 707/751 |
| 2013/0072765 A1* | 3/2013 | Kahn | A61B 5/01 600/301 |
| 2013/0138656 A1* | 5/2013 | Wheaton | G06F 17/30705 707/740 |
| 2013/0158367 A1* | 6/2013 | Pacione | E04F 13/06 600/301 |
| 2013/0216982 A1* | 8/2013 | Bennett | G09B 5/00 434/127 |
| 2014/0114889 A1* | 4/2014 | Dagum | G06F 19/3406 706/12 |
| 2014/0221791 A1* | 8/2014 | Pacione | A61B 5/7455 600/301 |
| 2015/0019710 A1* | 1/2015 | Shaashua | G06F 17/30705 709/224 |
| 2015/0019714 A1* | 1/2015 | Shaashua | H04L 67/24 709/224 |
| 2015/0033290 A1* | 1/2015 | Benyo | H04L 67/34 726/3 |
| 2015/0081210 A1* | 3/2015 | Yeh | G06F 19/3406 701/428 |
| 2015/0112899 A1* | 4/2015 | Dagum | A61B 5/6898 706/12 |
| 2015/0149207 A1* | 5/2015 | O'Keefe | G06F 19/3456 705/3 |
| 2015/0216413 A1* | 8/2015 | Soyao | A61B 5/0022 709/204 |
| 2015/0242468 A1* | 8/2015 | Shoemaker | G06F 17/30528 707/755 |
| 2015/0272473 A1* | 10/2015 | Zafiroglu | A61B 5/682 600/302 |
| 2015/0296247 A1* | 10/2015 | Glasser | H04L 65/4084 725/74 |
| 2015/0331711 A1* | 11/2015 | Huang | G06F 3/0481 719/320 |
| 2016/0012342 A1* | 1/2016 | Simon | G06N 5/048 706/52 |

* cited by examiner

AUTOMATIC APPLICATION-BASED EXERCISE TRACKING SYSTEM AND METHOD

CROSS-REFERENCE TO RELATED APPLICATIONS

This application is a continuation-in-part of U.S. application Ser. No. 15/041,780, filed 11 Feb. 2016, and claims the benefit of U.S. Provisional Application No. 62/193,879, filed 17 Jul. 2015, the disclosures of which are incorporated by reference herein.

BACKGROUND

Current application-based exercise tracking systems comprise software systems designed to run on mobile and other computing devices. These software systems are extremely tedious to use, all requiring a user to undergo the lengthy process in which that user must: i) input whether the exercise is a cardiovascular or strength training exercise, ii) type or voice transcribe (using the device microphone) the exercise name, iii) search for the exercise, iv) select the appropriate exercise from a list of options, v) input the exercise time, distance and/or resistance quantity(ies), and then repeat for every exercise in the workout to be tracked.

Importantly, to demonstrate the gross inefficiency of the aforementioned application-based exercise tracking systems one simply needs to add up the current number of steps generally required of users in order to track a workout that consists of one cardio exercise and four strength training exercises that have three sets each. That number is generally between an astounding fifty and one-hundred steps, depending on the system and the variability in exercises and sets, repetitions and weight. This is burdensome and inconvenient which detracts from the use of such systems.

The arrival of wearable fitness tracking devices to the exercise tracking market has provided a significantly more efficient method for those looking to track very general fitness activity levels than that which is provided by the current art of application-based exercise tracking systems. However, wearable fitness tracking devices are grossly inadequate in terms of the comprehensiveness of exercise data they collect and users looking to track more specifics about their workouts and exercises must still rely on the aforementioned application-based exercise tracking systems.

It is desirable to provide systems and methods that address the foregoing and other problems with known approaches, and it is to this that the present invention is directed. For the sake of clarity, exercise tracking can be defined as the process of logging an individual user's exercises completed (e.g. walking, bench press, crunches, yoga, etc.), including the associated time, distance or resistance numeric quantity(ies) (e.g. 2, 10, 35, etc.), time, distance or resistance quantity unit(s) (e.g. miles, minutes, sets and repetitions, etc.) and calories burned data for each exercise.

SUMMARY OF THE INVENTION

The invention described herein relates to an automatic application-based exercise tracking system and method. It provides a comprehensive automatic exercise tracking system and method that: i) enables the capture of significantly more exercise related information than that which is collected by wearable fitness devices; and ii) is significantly faster and more efficient to use than the current art in application-based exercise tracking. This is achieved by the invention through the automation of the complete application-based exercise tracking process. The current art in application-based exercise tracking is incapable of such complete automation and these systems require manual user input throughout much or all of the exercise tracking experience.

The diagrams and detailed description contained herein below provide a step by step look at methods, algorithms and processes of preferred embodiments of the invention that enable application-based automatic exercise tracking A summary will first provide a general overview of such methods, algorithms and processes with the details left to the detailed description of preferred embodiments below.

The present invention receives user-submitted input text describing an exercise such as by voice-transcribed or typed text and parses the input text into segments of parsed text. The exercise time, distance and/or resistance numeric quantity(ies) (e.g. 2, 10, 35, etc.), if any, may be removed from the parsed text and a multi-path unit database search may be done on the text to find an exercise time, distance and/or resistance quantity unit(s) (e.g. miles, minutes, sets and repetitions, etc.). If an exercise quantity unit(s) is found, it is tracked by the system along with the exercise numeric quantity(ies). If the parsed text does not contain an exercise numeric quantity the system may utilize user data history and entire user population data history lookups in assigning a most associated exercise numeric quantity to each such exercise quantity unit.

The remaining parsed text may be cleaned and a sequence of a user data history lookup and then an entire user population data history lookup may be performed, as necessary, to identify previous text match data to determine what exercise (E) (e.g. walking, bench press, crunches, yoga, etc.) should be tracked by the system. If no previous text matches are found, the system modifies the search strings for the parsed and cleaned text and then runs an exercise database search on such text. An entire user population data history lookup may be performed to find the total number of times each exercise search result has been tracked by the system, and that data along with an exercise search score may be used in a multi-rule process that results in an exercise text match scoring rank. The top ranked exercise may be selected as the exercise (E) tracked by the system.

If the parsed text does not contain a quantity unit (e.g. miles, minutes, sets and repetitions, etc.), then a user data history lookup followed by an entire user population data history lookup may be done, as necessary based on a multi-path process, to use previous quantity unit data associated with the exercise (E) identified to be tracked to determine what unit should be tracked by the system; or, if the parsed text contains an exercise quantity numeric value(s), a quantity unit may be assigned using exercise type and quantity numeric value sequence pattern recognition logic.

The invention utilizes machine learning with large, real-time user data sets, text aliasing logic and data that replaces certain text with aliased text that is appropriate (e.g. "raps" equals "reps") and quantity exceptions logic and data (e.g. 10 k, P90X, etc.) as part of the processes of enabling complete automatic exercise tracking.

The aforementioned innovative processes afforded by the invention provide automatic application-based exercise tracking for all exercise information submissions, including submissions that do not include an exercise numeric quantity and/or a quantity unit. This results in a vastly superior exercise tracking experience over the current art in application-based exercise tracking. Users need only a single exercise information submission for complete automatic exercise tracking of one or more exercises. The resulting efficiency provided to users of the invention enables them to track a workout that comprises, for instance, one cardio exercise and four strength training exercises that have three sets each in a mere three to nine steps, depending on variability in sets, repetitions and weight.

BRIEF DESCRIPTION OF THE DRAWINGS

In the course of the detailed description below, reference will be made to the attached drawings. These drawings illustrate different objects, aspects and advantages of the present invention, and also include reference numbers designating structures, components and elements present in the various embodiments illustrated. It is understood that various combinations of the structures, components and/or elements other than those specifically shown are also contemplated and are within the scope of the present invention.

Moreover, there are a number of different embodiments described and illustrated herein. The present invention is neither limited to any single aspect and/or embodiment, nor to any combinations and/or permutations of such aspects and/or embodiments. Moreover, each of the various aspects of the present invention, and/or embodiments thereof, may be employed alone or in combination with one or more of the other aspects and/or embodiments. For the sake of brevity, not all of the possible permutations and combinations are discussed and/or illustrated separately herein.

DETAILED DESCRIPTION OF PREFERRED EMBODIMENTS

Figure 1:
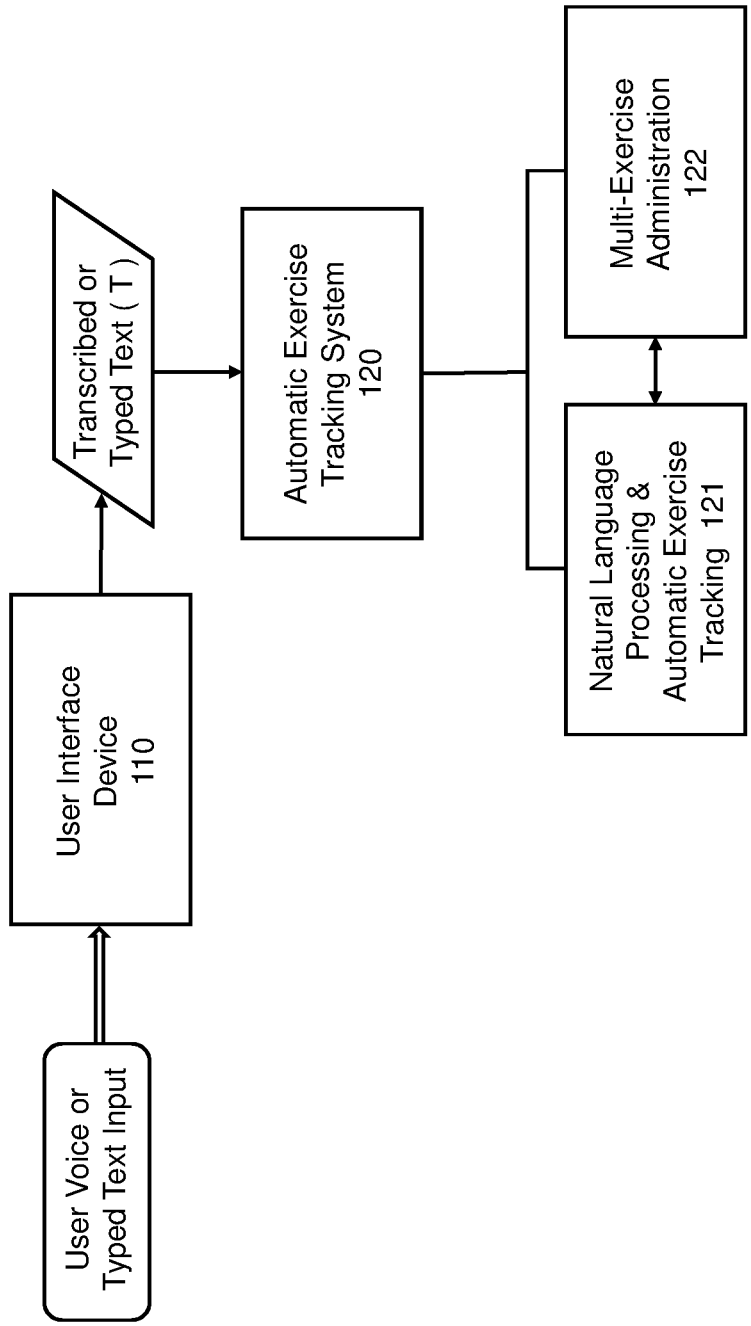
FIG. 1 is a block diagram of the architecture of an automatic application-based exercise tracking system in accordance with a preferred embodiment of the invention.

In a preferred embodiment, an exercise tracking system in accordance with the invention may be integrated with a mobile phone, tablet, laptop, desktop, smartwatch, wearable device or other computing system. FIG. 1 is a block diagram showing the top-level architecture of the automatic application-based exercise tracking system which illustrates that a user of the system inputs exercise tracking information as input text via voice or typed text into the user interface device 110, which may be associated with a mobile phone, tablet, laptop, desktop, smartwatch, wearable device or other computing system that comprises an automatic application-based exercise tracking system 120 in accordance with the invention. The system may comprise a processor and executable instructions embodied in computer readable media (not shown explicitly) for controlling the processor to perform the operations described herein, and may have associated data storage, also not shown. For voice inputs, the user interface device 110 may transcribe the voice input to produce text (T). Text (T) may also be input manually as typed text by a user via a user interface device 110. The voice-transcribed or typed text (T) enters the automatic application-based exercise tracking system 120. Voice-transcribed or typed text (T) from the exercise tracking system 120 may be provided to a multi-exercise administration component 122 and to a natural language processing and automatic exercise tracking component 121 for processing.

Figure 2:
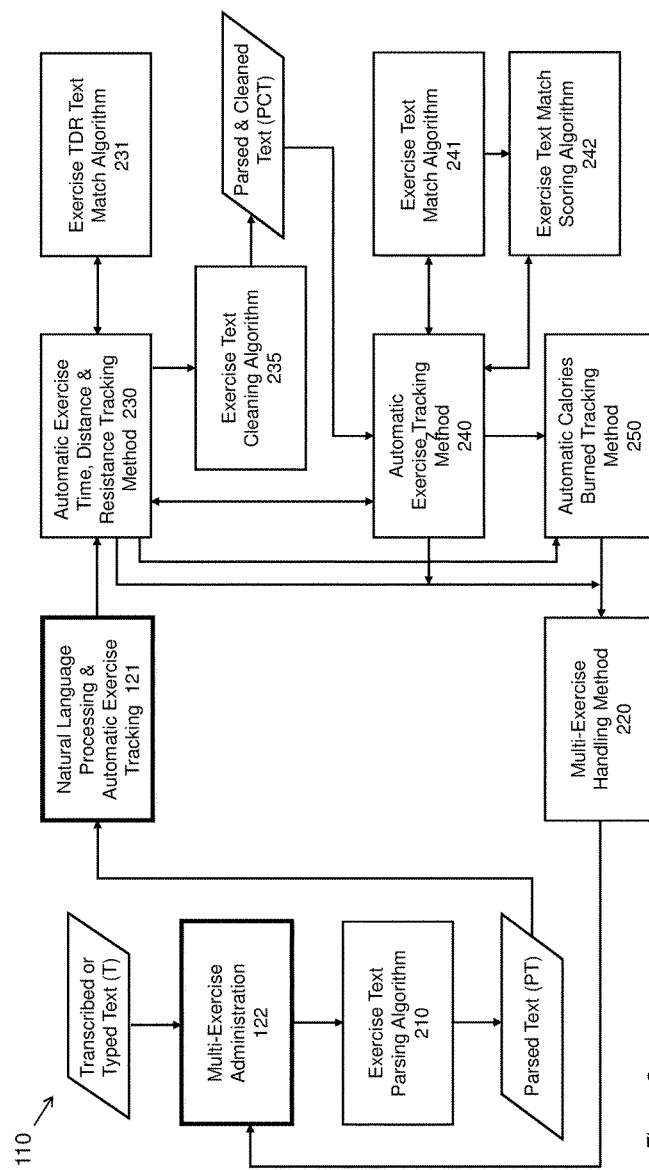
FIG. 2 is a block diagram of the architecture of an embodiment of a multi-exercise administration and natural language processing and automatic application-based exercise tracking system shown in FIG. 1.

FIG. 2 is a block diagram showing the architecture of an embodiment of the multi-exercise administration component 122 and the natural language processing and automatic exercise tracking component 121, and illustrates how voice-transcribed or typed input text (T) enters and is processed therein. The voice-transcribed or typed text (T) first is provided to the multi-exercise administration component and is processed by the exercise text parsing algorithm 210, which then delivers parsed text (PT) to the natural language processing and automatic exercise tracking component 121. The natural language processing and automatic exercise tracking component 121 may first process the parsed text (PT) using an automatic exercise time, distance and resistance tracking method 230, which utilizes an exercise TDR text match algorithm 231 (described below), to produce the exercise time, distance and/or resistance quantity numeric value(s) (QN) and the exercise time, distance and/or resistance quantity unit(s) (QU) to be tracked for each specific exercise in the applicable parsed text (PT). The parsed text (PT) is stripped of any exercise quantity numeric value(s) (QN) and quantity unit(s) (QU) found by the automatic exercise time, distance and resistance tracking method 230, and the resulting parsed text (PT) without QN and QU ($PT_{WNU}$) may be delivered to an exercise text cleaning algorithm 235. The exercise text cleaning algorithm 235 generates parsed and cleaned text (PCT) for each segment of $PT_{WNU}$ and passes each such segment of PCT into an automatic exercise tracking method 240. The automatic exercise tracking method 240, which utilizes the exercise text match algorithm 241 and the exercise text match scoring algorithm 242 (described below), produces the specific exercise (E) to be tracked by the system for each segment of parsed and cleaned text (PCT) and then passes such exercise (E) back to an automatic exercise time, distance and resistance tracking method 230 for use therein in completion of its processes. Each generated exercise (E) and associated exercise quantity numeric value(s) (QN) and exercise quantity unit(s) (QU) is then passed to an automatic calories burned tracking method 250 which attaches applicable calories burned data to each such exercise and exercise quantity numeric value(s) (QN) and exercise quantity unit(s) (QU). Each exercise name and associated QN and QU and applicable calories burned data are sent to a multi-exercise handling method 220, which keeps all exercises and related data organized and properly associated with the proper segments of the parsed text (PT) for exercise quantity numeric value(s) (QN) and quantity unit(s) (QU) and parsed and cleaned text (PCT) for exercise name for delivery back to the user interface device 110. The multi-exercise handling method 220 may be part of the multi-exercise administration component 122.

Figure 3:
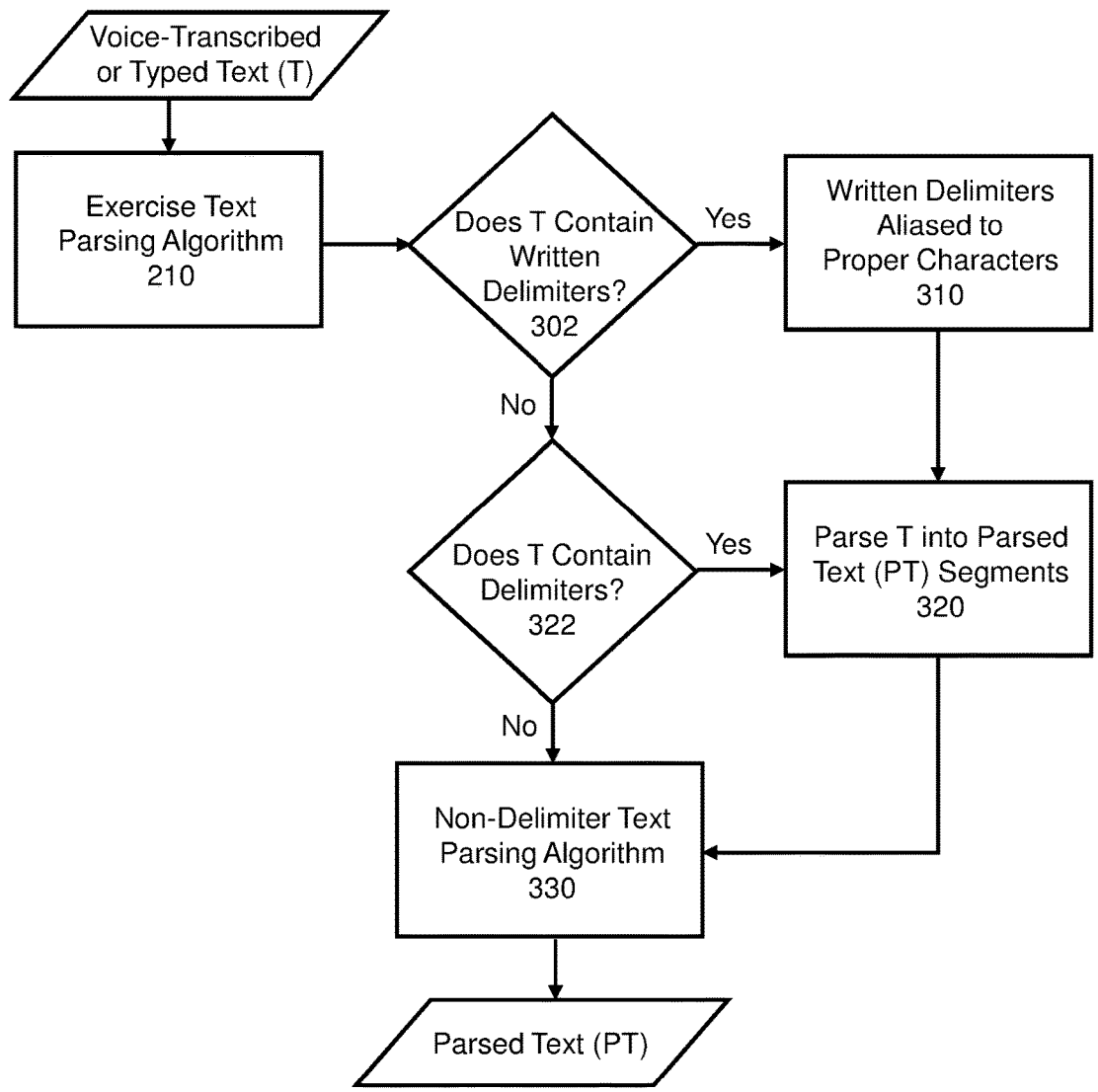
FIG. 3 is a flow diagram showing the steps performed by an embodiment of an exercise text parsing algorithm shown in FIG. 2.

FIG. 3 is a flow diagram showing the steps performed by an embodiment of the exercise text parsing algorithm 210 shown in FIG. 2. The purpose of the exercise text parsing algorithm 210 is to produce parsed text (PT) from the voice-transcribed or typed text (T). FIG. 3 shows that the voice-transcribed or typed text (T) may be first analyzed to determine at 302 if any written delimiters (e.g. "comma", "semi-colon", etc.) are found; if present, such written delimiters are aliased to proper characters (e.g. "," ";") in process 310 of FIG. 3 and then the voice-transcribed or typed text (T) is parsed into parsed text (PT) segments in process 320 of FIG. 3. If written delimiters are not found in the text, the algorithm determines at 322 if any character delimiters are present; if character delimiters are found, then the voice-transcribed or typed text (T) is parsed into parsed text (PT) segments in process 320 of FIG. 3. The parsed text (PT) segments created in process 320 of FIG. 3 are then delivered into a non-delimiter text parsing algorithm 330 (described herein below) for further parsing, if any. If character delimiters are not found, then the voice-transcribed or typed text (T) is delivered to the non-delimiter text parsing algorithm 330. The non-delimiter text parsing algorithm 330 outputs the fully processed segments of parsed text (PT) for all parsed text (PT) segments and voice-transcribed or typed text (T) that have been inputted therein.

The following is a description of a preferred embodiment of the exercise text parsing algorithm 210:

i. If T contains written delimiters (e.g. "comma", "semi-colon", etc.), Then alias written delimiter to the proper character (e.g. "," ";");
   If T contains one or more delimiters (including aliased delimiters), Then parse T as specified by such delimiters into PT segments and run such PT segments through the non-delimiter text parsing algorithm to produce additional PT segments, if any;
   Else, run T through the non-delimiter text parsing algorithm to produce one or more PT segments.

ii. Definitions of terms in the foregoing exercise text parsing algorithm 210 are:
   a. T = user-submitted voice-transcribed or typed input text
   b. PT=T that has been parsed into one or more parsed text segments The following is a description of an embodiment of the non-delimiter text parsing algorithm 330:

i. If T contains more than one word,
      Then the Viterbi algorithm processes T, utilizing TMD to produce $VP_{(1 \ldots N)}$;
      If $VP_1$ is higher ranked than T, then each such $VP_1$ is a PT;
      Else, T=PT.
   Else, T=PT.
   If PT contains more than one word and one or more DW,
      Then the Viterbi algorithm processes PT, utilizing TMD to produce $VP_{(1 \ldots N)}$;
      If $VP_1$ is higher ranked than PT, then each segment of such $VP_1$ is a PT;
      Else, PT=PT.
   Else, PT =PT.

ii. Definitions in this algorithm are:
   a. T=user-submitted voice-transcribed or typed text
   b. PT=T that has been parsed into one or more parsed text segments
   c. TMD=user and entire user population data history for PT matches
   d. $VP_{(1 \ldots N)}$=each Viterbi parse, where $VP_1$ is the top ranked (most likely) parse for any given T or PT
   e. DW=delimiting words, including "with", "and" and "or"

Figure 4A:
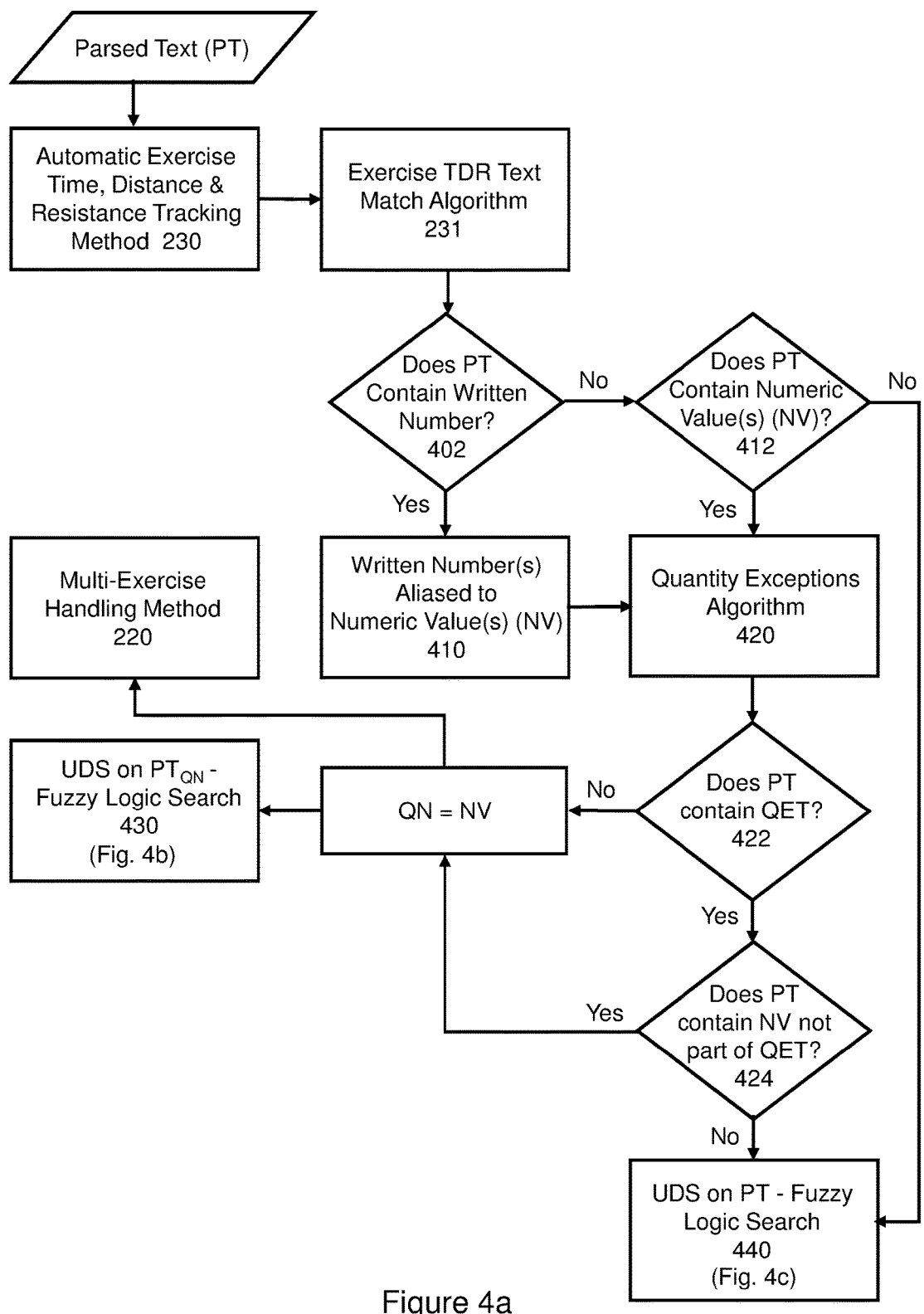
FIG. 4a is a flow diagram showing the first steps performed by an embodiment of an automatic exercise time, distance and resistance tracking method, including an exercise TDR text match algorithm, shown in FIG. 2.

FIG. 4a is a flow diagram showing the first steps that may be performed by the automatic exercise time, distance and resistance tracking method 230, including the exercise TDR text match algorithm 231, shown in FIG. 2. The purpose of the automatic exercise time, distance and resistance tracking method 230 is to find and track the exercise time, distance and/or resistance numeric quantity(ies) and quantity unit(s) for the exercise in each parsed text (PT) segment. FIG. 4a shows that the exercise TDR text match algorithm 231 first determines at 402 whether parsed text (PT) contains any written numbers, i.e., textual numbers, if one or more written numbers is found, such written number(s) is aliased to the proper numeric value(s) (NV) in process 410 of FIG. 4a. If a written number is not present, then the algorithm determines at 412 if a numeric value(s) (NV) is present. If a numeric value (NV) is not found, then a fuzzy logic unit database search (UDS) 440 may be run, using text aliasing (e.g. "raps" equals "reps"), to find a matching exercise time, distance and/or resistance quantity unit(s) (QU) within the parsed text (PT). If one or more numeric values (NV) is found or a written number(s) has been passed through the aliasing process 410 of FIG. 4a, then the parsed text (PT) may be processed using a quantity exceptions algorithm 420. If one or more quantity exception terms (QET) (e.g. 10 k, P90X, etc.), including any written or numeric value forms (e.g. ten k, p ninety x, etc.), that contain NV is found and the parsed text (PT) does not contain any numeric values (NV) that are not part of a quantity exception term (QET), then the fuzzy logic unit database search (UDS) 440 may be run, using text aliasing, to find a matching exercise quantity unit(s) (QU) within the parsed text (PT). If a quantity exception term (QET) is not found at 422 or a numeric value(s) (NV) that is not part of a quantity exception term (QET) is found at 424, then the exercise time, distance and/or resistance quantity numeric value(s) (QN) is set equal to the numeric value(s) (NV) in the parsed text (PT), the quantity numeric value(s) (QN) is sent to the multi-exercise handling method 220, and the fuzzy logic unit database search (UDS) 430 may be run, using text aliasing (e.g. "raps" equals "reps"), to find a matching exercise time, distance and/or resistance quantity unit(s) (QU) with the word directly after each QN in the sequence of words in PT (PT$_{QN}$). It is understood that parsed text (PT) may contain and an exercise may have more than one NV and more than one QN (e.g. bench press 10 reps of 185 lbs).

Figure 4B:
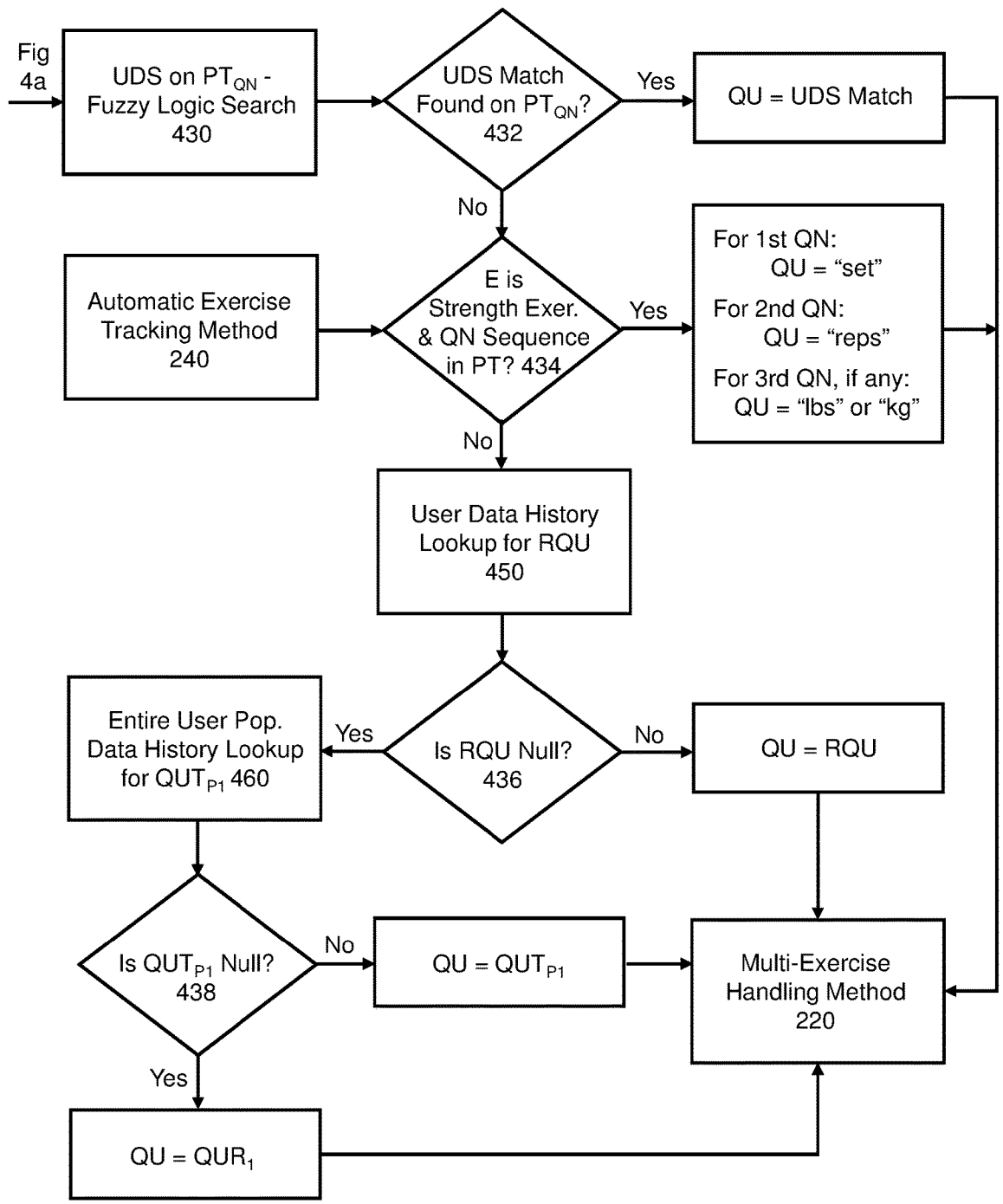
FIG. 4b is a flow diagram showing further steps performed by the automatic exercise time, distance and resistance tracking method, including an exercise TDR text match algorithm, shown in FIG. 2.

The following is a description of an embodiment of the quantity exceptions algorithm 420:
  i. Run database lookup for PT against QETL;
     If PT contains one or more QET and such QET does not contain a NV that is not part of such QET, Then NV is not QN;
     Else, NV=QN.
  ii. Definitions of terms in this algorithm are:
     a. QET =a quantity exception term (e.g. 10 k, P90X, etc.), including any written or numeric value forms (e.g. ten k, p ninety x, etc.), that contains a numeric value
     b. QETL=the list of all QET
     c. PT=user-submitted voice-transcribed or typed text that has been parsed by the exercise text parsing algorithm
     d. NV=a numeric value, including any aliased numeric value, found in PT
     e. QN=exercise time, distance and/or resistance quantity numeric value FIG. 4b is a continuation of the process flow diagram of FIG. 4a and shows further steps performed by the automatic exercise time, distance and resistance tracking method 230, including the exercise TDR text match algorithm 231, shown in FIG. 2. If an exercise time, distance and/or resistance quantity unit (QU) match(es) is found at 432 from the unit database search (UDS) 430 on the word directly after each QN in the sequence of words in the parsed text PT (PT$_{QN}$), then the exercise time, distance and/or resistance quantity unit(s) (QU) is the UDS match(es), and each such QU is sent to the multi-exercise handling method 220. If no match is found, then the automatic exercise tracking method 240 from FIG. 2 may be invoked to get the exercise type, which may be either: i) cardiovascular; ii) strength training; or iii) flexibility, for the exercise to be tracked (E) (e.g. walking, bench press, crunches, yoga, etc.) for the resulting parsed and cleaned text (PCT) from such parsed text (PT). It is then determined at 434 if both: i) the exercise is a strength training exercise type; and ii) if a sequence pattern of "QNxQNxQN" or "QNxQN" (QN is the exercise quantity numeric value(s) and the letter "x" separates each QN; spaces between each QN and "x" may also be present) is found in the parsed text (PT). If at 434 it is found that the exercise to be tracked (E) is a strength training exercise type and such a sequence pattern is found, then the exercise quantity units (QU) are equal to: i) "set" for the first QN in the sequence; ii) "reps" for the second QN in the sequence; and iii) "lbs" or "kg" (as determine based on user settings) for the third QN in the sequence, if any; and such exercise quantity units (QU) are sent to the multi-exercise handling method 220. If at 434 it is found that the exercise to be tracked (E) is not a strength training exercise type or such a sequence pattern is not found, then a user data history lookup for the most recently tracked exercise time, distance and/or resistance quantity unit(s) (QU) for the exercise to be tracked (E) by the user (RQU) may be run at 450, and if RQU is found at 436, then the exercise time, distance and/or resistance quantity unit(s) (QU) is each such RQU and such exercise quantity unit(s) (QU) is sent to the multi-exercise handling method 220. If the user data history lookup for RQU is null at 436, then an entire user population history lookup for the exercise time, distance and/or resistance quantity unit(s) (QU) tracked most often for the exercise to be tracked (E) by the entire user population (QUT$_{P1}$) may be run at 460; if QUT$_{P1}$ is found at 438, then the exercise time, distance and/or resistance quantity unit(s) (QU) is such QUT$_{P1}$ and such exercise quantity unit(s) (QU) is sent to the multi-exercise handling method 220. If the entire user population history lookup for QUT$_{P1}$ is null at 438, then the exercise time, distance and/or resistance quantity unit(s) (QU) is set equal to the top ranking exercise quantity unit(s) associated in the system with the exercise to be tracked (E) (QUR$_1$) and such exercise quantity unit(s) (QU) is sent to the multi-exercise handling method 220.

Figure 4C:
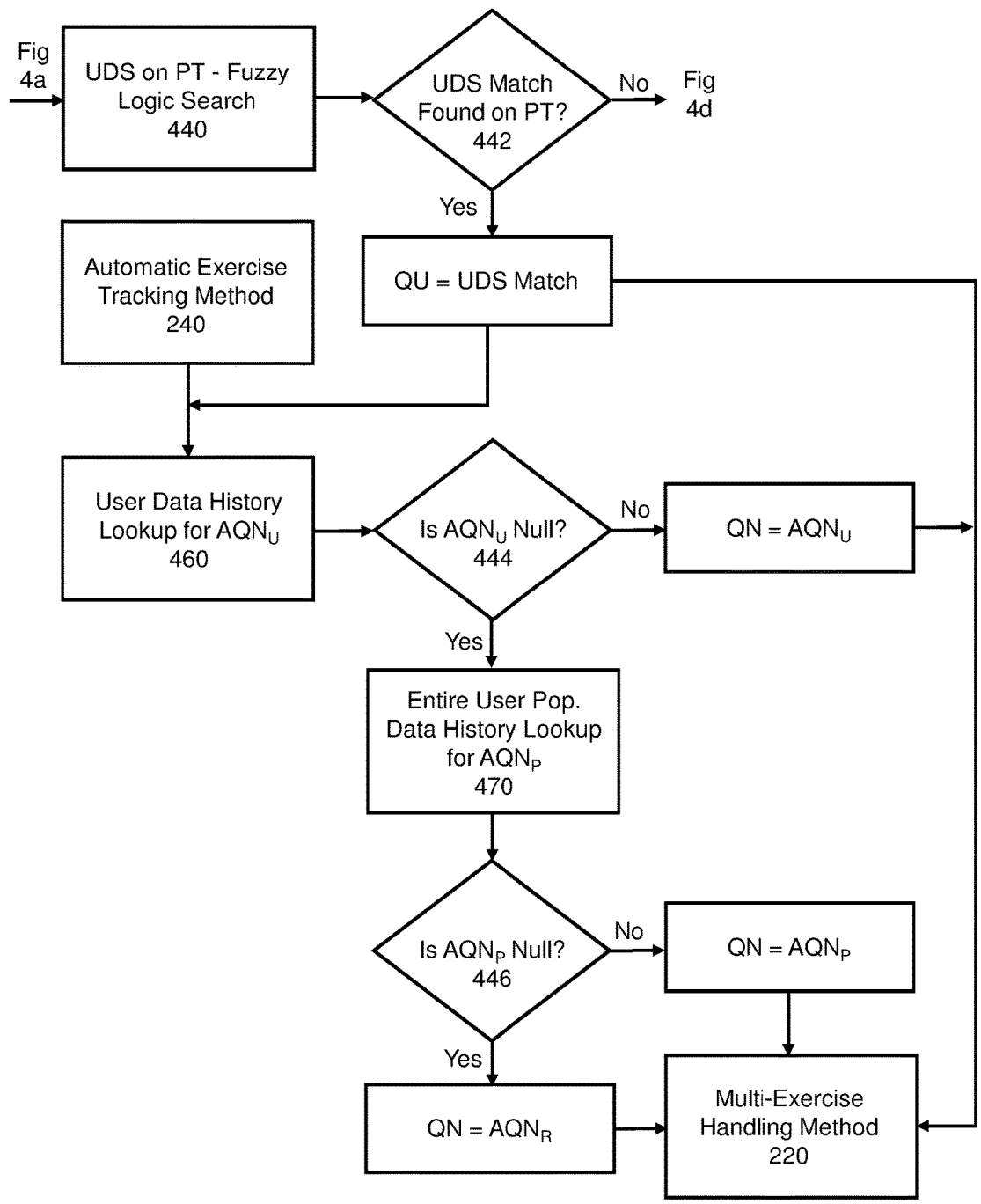
FIG. 4c is a flow diagram showing further steps performed by the automatic exercise time, distance and resistance tracking method, including an exercise TDR text match algorithm, shown in FIG. 2.

FIG. 4c is a continuation of the process flow diagram of FIG. 4a and shows further steps performed by the automatic exercise time, distance and resistance tracking method 230, including the exercise TDR text match algorithm 231, shown in FIG. 2. If an exercise time, distance and/or resistance quantity unit(s) (QU) match is found at 442 from the unit database search (UDS) 440 on the parsed text (PT), then the exercise quantity unit(s) (QU) is the UDS match(es) and each such QU is sent to the multi-exercise handling method 220. The automatic exercise tracking method 240 from FIG. 2 may be invoked to get the exercise to be tracked (E) (e.g. walking, bench press, crunches, yoga, etc.) by the user for the resulting parsed and cleaned text (PCT) from such parsed text (PT). A user data history lookup for such exercise quantity unit(s) (QU) UDS match(es) for the exercise to be tracked (E) may be run at 460 and if such QU is found then the exercise time, distance and/or resistance quantity numeric value (QN) for each such QU is the most often associated QN for each such QU (AQN$_U$) as determined at 444; and each QN is sent to the multi-exercise handling method 220. If the user data history lookup for AQN$_U$ is null at 444, then an entire user population history lookup for such QU for the exercise to be tracked (E) may be run at 470 and if such QU is found then the exercise time, distance and/or resistance quantity numeric value (QN) for each such QU is the most often associated QN for each such QU (AQN$_P$) as determined at 446; and each QN is sent to the multi-exercise handling method 220. If the entire user population history lookup for AQN$_P$ is null at 446, then the exercise time, distance and/or resistance quantity numeric value (QN) for each such QU is the highest ranked QN for each such QU from tracking data for all exercises (AQN$_R$); and each QN is sent to the multi-exercise handling method 220.

Figure 4D:
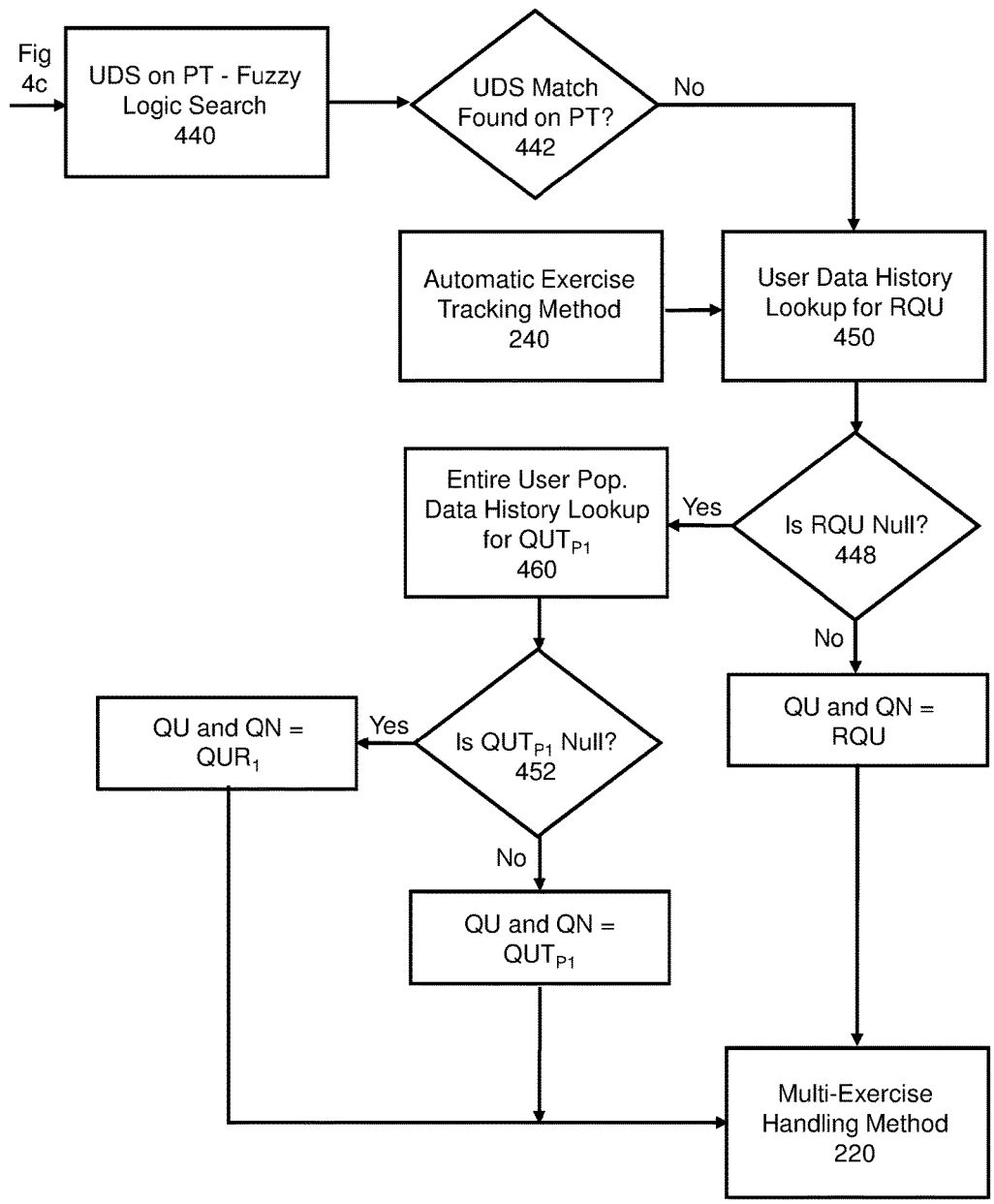
FIG. 4d is a flow diagram showing further steps performed by the automatic exercise time, distance and resistance tracking method, including an exercise TDR text match algorithm, shown in FIG. 2.

FIG. 4d is a continuation of the process flow diagram of FIG. 4a and FIG. 4c and shows further steps performed by the automatic exercise time, distance and resistance tracking method 230, including the exercise TDR text match algorithm 231, shown in FIG. 2. If no match is found at 442 from the unit database search (UDS) 440, the automatic exercise tracking method 240 from FIG. 2 may be invoked to get the exercise to be tracked (E) (e.g. walking, bench press, crunches, yoga, etc.) by the user for the resulting parsed and cleaned text (PCT) from such parsed text (PT). A user data history lookup for the most recently tracked exercise time, distance and/or resistance quantity unit(s) (QU), including the most often associated QN for each such QU, for the exercise to be tracked (E) by the user (RQU) may be run at 450, and if a RQU is found at 448, then the exercise time, distance and/or resistance quantity unit(s) (QU) is such RQU and such exercise quantity unit(s) (QU), including the most often associated QN for each such QU, are sent to the multi-exercise handling method 220. If the user data history lookup for RQU is null at 448, then an entire user population history lookup for the exercise time, distance and/or resistance quantity unit(s) (QU) tracked most often, including the most often associated QN for each such QU, for the exercise to be tracked (E) by the entire user population ($QUT_{P1}$) may be run at 460; if $QUT_{P1}$ is found at 452, then the exercise time, distance and/or resistance quantity unit(s) (QU) is such $QUT_{P1}$ and such exercise quantity unit(s) (QU), including the most often associated QN for each such QU, are sent to the multi-exercise handling method 220. If the entire user population history lookup for $QUT_{P1}$ is null at 452, then the exercise time, distance and/or resistance quantity unit(s) (QU) is set equal to the top ranking exercise quantity unit(s) associated in the system with the exercise to be tracked (E), including the most often associated QN for each such QU, ($QUR_1$) and such exercise quantity unit(s) (QU), and the most often associated QN for each such QU, are sent to the multi-exercise handling method 220.

The following is a description of an embodiment of the exercise TDR text match algorithm 231:

i. If PT contains written number, Then alias written number(s) to correct NV;
  If PT contains NV (including aliased NV), Then run PT through the quantity exceptions algorithm;
  If PT does not contain NV or QET is not null and PT does not contain NV that is not part of QET, then perform UDS on PT;
    If UDS match(es) found for PT, Then QU=UDS match;
      Get E from automatic exercise tracking method;
      Run user data history lookup for $AQN_U$;
      QN=$AQN_U$;
      If $AQN_U$ is Null, Then run entire user population data history lookup for $AQN_P$;
      QN=$AQN_P$;
      If $AQN_P$ is Null, Then QN=$AQN_R$.
    If UDS match(es) not found for PT, then get E from automatic exercise tracking method and run user data history lookup for RQU;
      QU and QN=RQU;
      If RQU is Null, Then run entire user population data history lookup for $QUT_{P1}$;
      QU and QN=$QUT_{P1}$;
      If $QUT_{P1}$ is Null, Then QU and QN=$QUR_1$.
  If PT contains NV and QET is null or PT with QET contains NV that is not part of QET, Then QN =NV and perform UDS on $PT_{QN}$ (fuzzy logic search using proprietary aliasing);
    If UDS match(es) found for $PT_{QN}$, Then QU=UDS match.
    If UDS match(es) not found for $PT_{QN}$, then get E from automatic exercise tracking method;
      If E is a strength training exercise type and sequence pattern of "QNxQNxQN" or QNxQN" is found in PT, then QU ="set" for the first QN in such sequence; QU="reps" for the second QN in such sequence; and QU ="lbs" or "kg" (as determined by user settings) for the third QN in such sequence, if any;
      Else, run user data history lookup for RQU;
      QU=RQU;
      If RQU is Null, Then run entire user population data history lookup for $QUT_{P1}$;
      QU=$QUT_{P1}$;
      If $QUT_{P1}$ is Null, Then QU=$QUR_1$ ii. Definitions of terms are:
  a. PT=user-submitted voice-transcribed or typed text that has been parsed by the exercise text parsing algorithm
  b. NV=a numeric value, including any aliased numeric value, found in PT
  c. QET =a quantity exception term (e.g. 10 k, P90X, etc.), including any written or numeric value forms (e.g. ten k, p ninety x, etc.), that contains a NV
  d. QU=exercise time, distance and/or resistance quantity unit
  e. UDS=Unit database search, using proprietary aliasing, for matching QU
  f. QN=exercise time, distance and/or resistance quantity numeric value
  g. E=an exercise (e.g. walking, bench press, crunches, yoga, etc.) to be tracked by the system
  h. $PT_{QN}$=the word directly after each QN in the sequence of words in PT
  i. $AQN_U$=the most often associated QN for each such QU, that is a UDS match, tracked for E by user, if any
  j. $AQN_P$=the most often associated QN for each such QU, that is a UDS match, tracked for E by the entire use population
  k. $AQN_R$=the highest ranked QN for each such QU, that is a UDS match, using tracking data for all exercises, using 1 if no QN found
  l. RQU=most recently tracked QU, and most often associated QN, if needed, for each such QU, for E by user, if any
  m. $QUT_{P1}$=QU, and the most often associated QN, if needed, for each such QU, tracked most often for E by entire user population
  n. $QUR_{(1 \ldots N)}$=all QU that are associated in the system with E in ranked order (e.g. $QUR_1$ is the highest ranked quantity unit for E), and the most often associated QN, if needed, for each such QU (ranking determined by presets at time of E creation)

Figure 5:
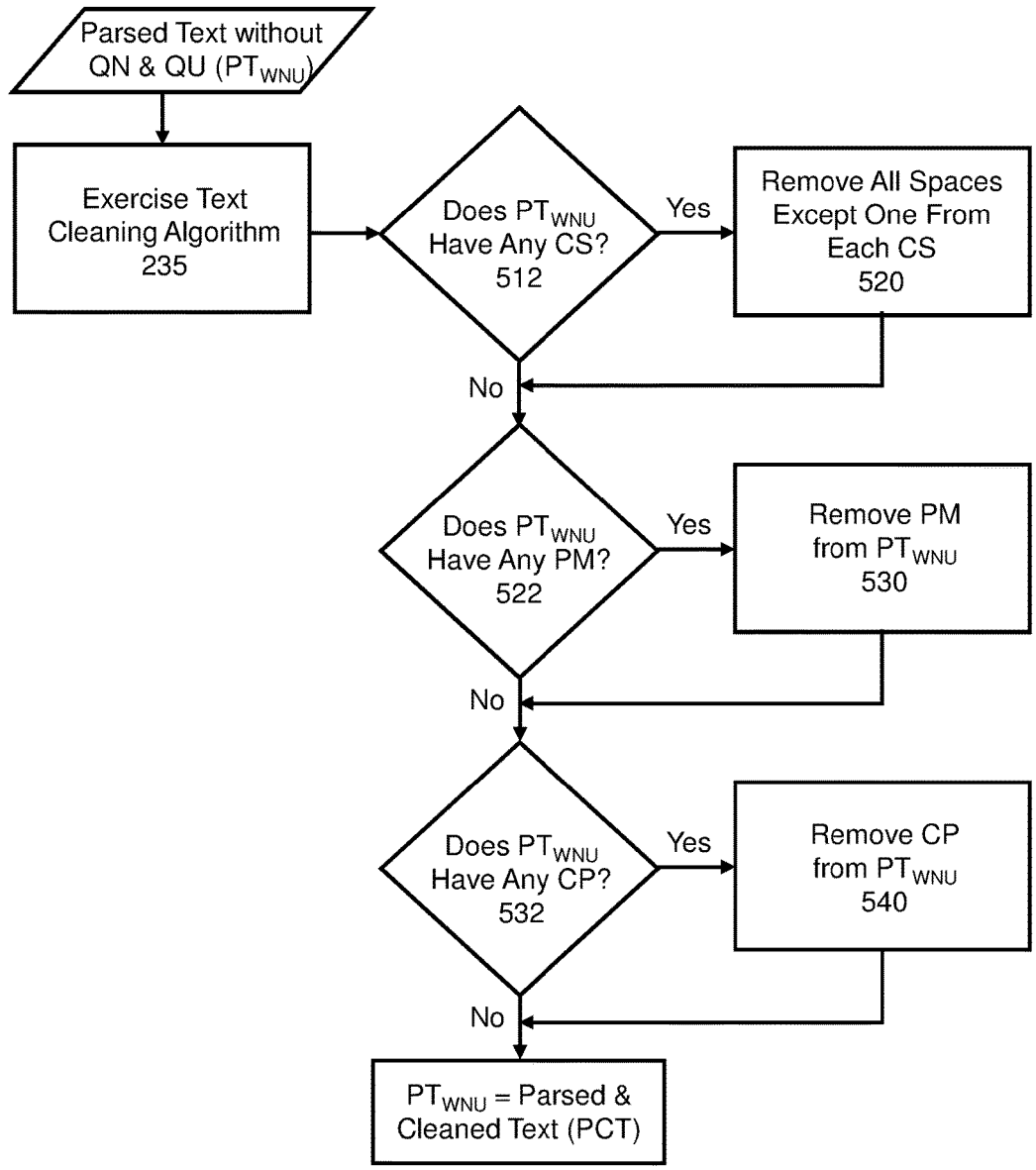
FIG. 5 is a flow diagram showing the steps performed by an embodiment of an exercise text cleaning algorithm shown in FIG. 2.

FIG. 5 illustrates the steps performed by a preferred embodiment of the exercise text cleaning algorithm 235 shown in FIG. 2 that removes words, connected spaces, and punctuation that are not used to identify exercises to produce parsed cleaned text. FIG. 5 shows that the parsed text without exercise time, distance and/or resistance quantity numeric value(s) (QN) and exercise time, distance and/or resistance quantity unit(s) (QU) ($PT_{WNU}$) enters the exercise text cleaning algorithm 235 and is analyzed at 512 to determine if any connected spaces (CS) are found; if present, the system then removes all spaces except one space from each set of connected spaces (i.e., a space symbol followed by one or more space symbol) (CS) in process 520 of FIG. 5. If connected spaces are not found or the $PT_{WNU}$ has been through process 520 of FIG. 5, the system then determines at 522 if the $PT_{WNU}$ has any extraneous punctuation (PM) such as periods, question marks, underscores, dashes and symbols not used in the exercise names; if present, the system removes any such PM from the $PT_{WNU}$ in process 530 of FIG. 5. If PM are not found or the $PT_{WNU}$ has been through process 530 of FIG. 5, the system then determines at 532 if the $PT_{WNU}$ has any specific conjunctions and/or prepositions at the beginning of each segment of $PT_{WNU}$ (CP); if present, the system removes any such CP from $PT_{WNU}$ in process 540 of FIG. 5. If CP are not found or the $PT_{WNU}$ has been through process 540 of FIG. 5, then the $PT_{WNU}$ is equal to the parsed and cleaned text (PCT).

Figure 6:
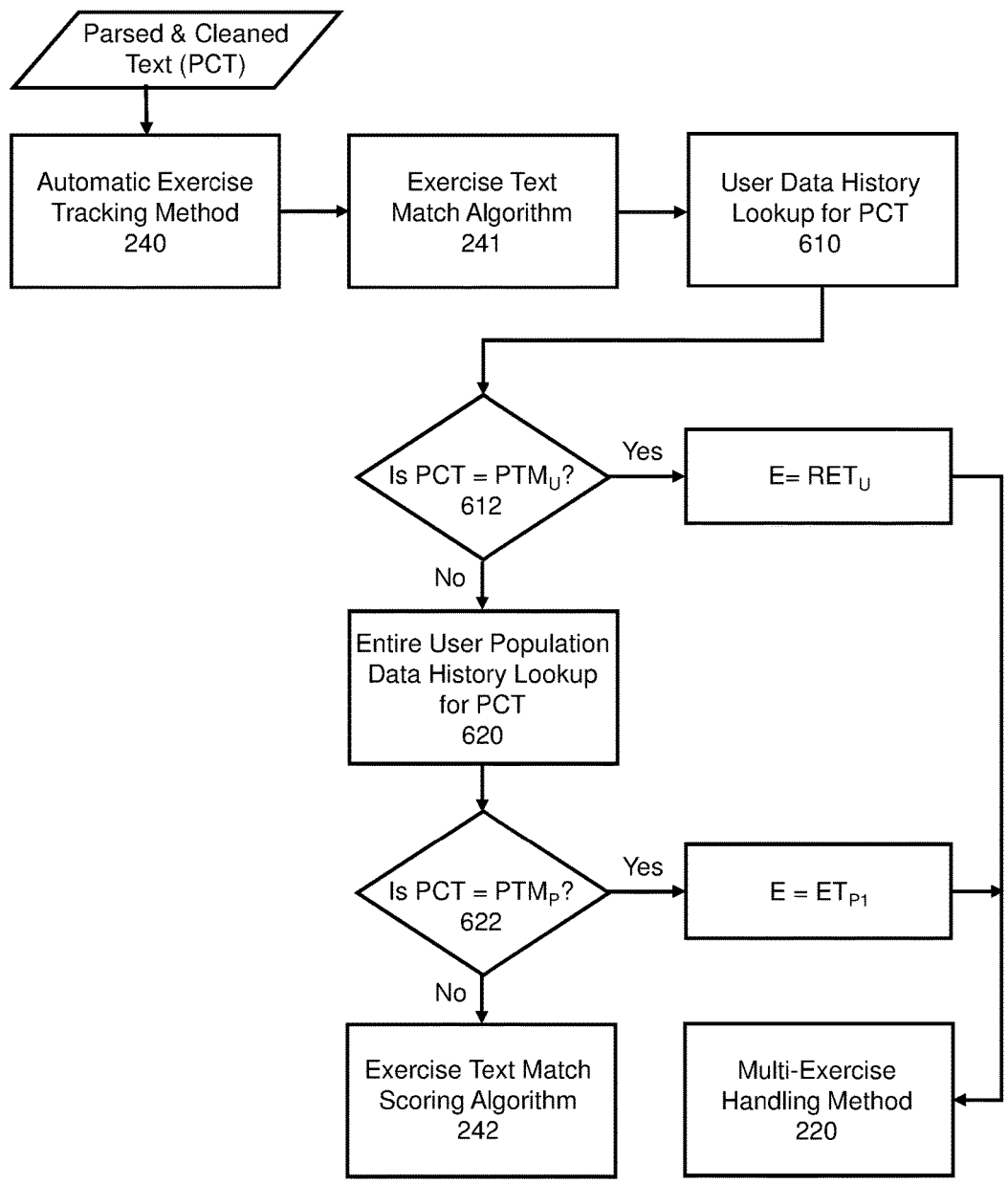
FIG. 6 is a flow diagram showing the steps performed by an embodiment of an automatic exercise tracking method, including the exercise text match algorithm, shown in FIG. 2.

The following is a description of an embodiment of the exercise text cleaning algorithm 235:
  i. Run $PT_{WNU}$ through exercise name aliasing system;
     If $PT_{WNU}$ has CS, Then remove from $PT_{WNU}$ all spaces except one space from each CS;
     If $PT_{WNU}$ has PM, Then remove PM from $PT_{WNU}$;
     If the $PT_{WNU}$ has CP, Then remove CP from $PT_{WNU}$;
     $PT_{WNU}$=PCT.
  ii. Definitions of terms are:
     a. $PT_{WNU}$=parsed text (PT) that has had the exercise time, distance and/or resistance quantity numeric value(s) (QN) and exercise time, distance and/or resistance quantity unit(s) (QU), if any, removed
     b. CS=connected spaces in $PT_{WNU}$
     c. PM=all periods, question marks, underscores, dashes and symbols not used in the exercise names in $PT_{WNU}$
     d. CP=specific conjunctions and/or prepositions at the beginning of each $PT_{WNU}$ segment
     e. PCT=parsed text without exercise time, distance and/or resistance quantity numeric value(s) (QN) and exercise time, distance and/or resistance quantity unit(s) (QU) ($PT_{WNU}$) that has been cleaned by the exercise text cleaning algorithm FIG. 6 is a flow diagram showing the steps performed by a preferred embodiment of the exercise text match algorithm 241 as part of the automatic exercise tracking method 240 shown in FIG. 2. The purpose of the automatic exercise tracking method 240 is to find and track the exercise in each parsed and cleaned text (PCT) segment. FIG. 6 shows that the exercise text match algorithm 241 first runs a user data history lookup on the parsed and cleaned text (PCT) for previous matches for such user ($PTM_U$) 610; if matches are found at 612, then the exercise (e.g. walking, bench press, crunches, yoga, etc.) to be tracked (E) is set equal to the most recent exercise tracked for submission $PTM_U$ ($RET_U$) and such exercise to be tracked (E) is sent to the multi-exercise handling method 220. If a match is not found, then an entire user data history lookup for previous matches of the parsed and cleaned text (PCT) is performed using data from the entire user population ($PTM_P$) 620; if matches are found, then the exercise to be tracked (E) is the exercise tracked most often by the entire user population for submission $PTM_P$ ($ET_{P1}$) and such exercise to be tracked (E) is sent to the multi-exercise handling method 220. If a match is not found at 622, the process moves to the exercise text match scoring algorithm.

Figure 7:
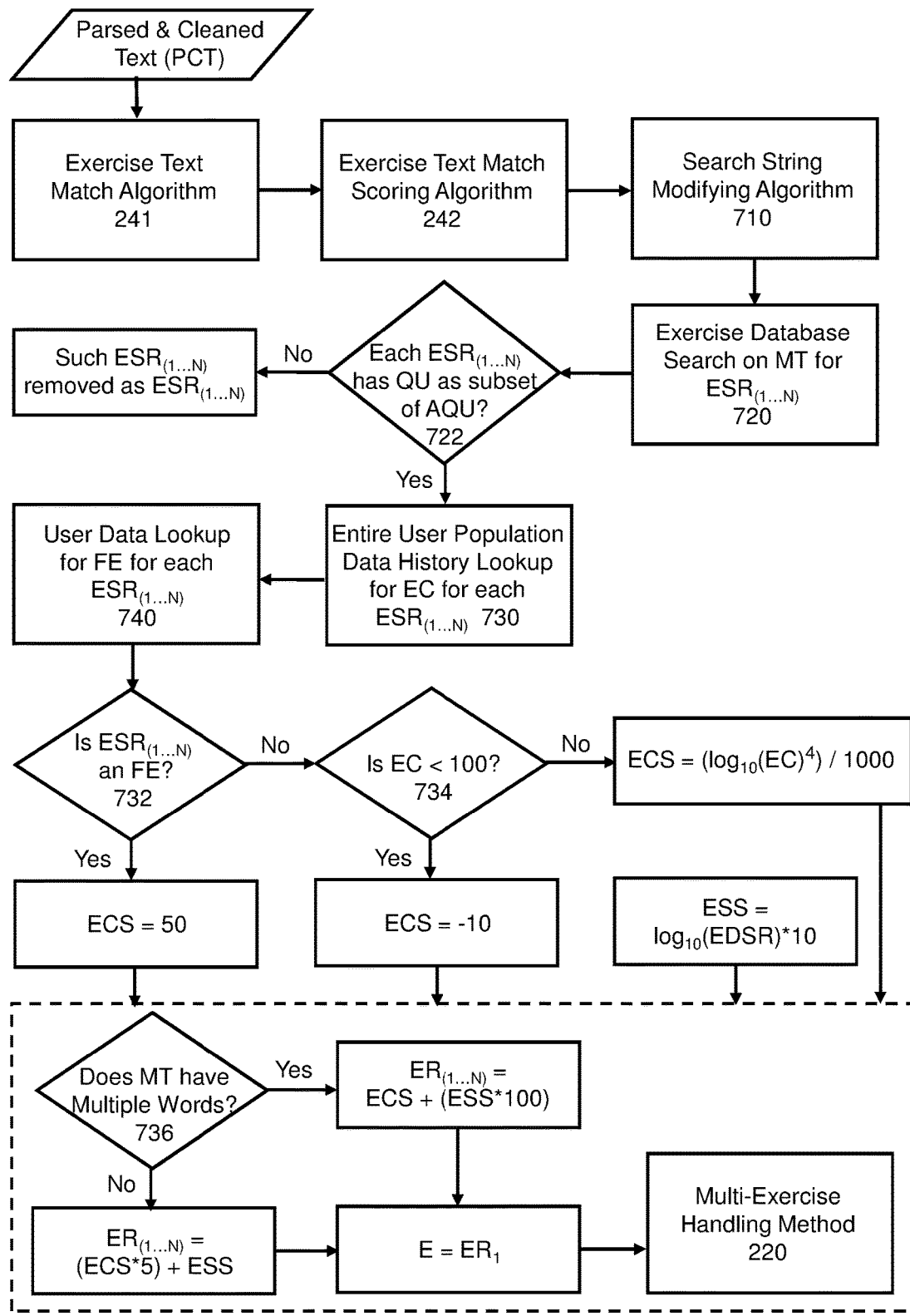
FIG. 7 is a flow diagram showing the steps performed by an embodiment of an exercise text match scoring algorithm shown in FIG. 2.

The following is a description of an embodiment of the exercise text match algorithm 241:
  i. Run user data history lookup for PCT;
     If PCT=$PTM_U$, Then E=$RET_U$;
     If PCT≠$PTM_U$, run entire user population data history lookup for PCT;
     If PCT=$PTM_P$, Then E=$ET_{P1}$;
     Else GoTo exercise text match scoring algorithm.
  ii. Definitions of terms are:
     a. PCT=parsed text without exercise time, distance and/or resistance quantity numeric value(s) (QN) and exercise time, distance and/or resistance quantity unit(s) (QU) ($PT_{WNU}$) that has been cleaned by the exercise text cleaning algorithm
     b. E=an exercise (e.g. walking, bench press, crunches, yoga, etc.) to be tracked by the system
     c. $PTM_U$=previous PCT matches for a user
     d. $RET_U$=most recent exercise tracked for submission $PTM_U$ by the user
     e. $PTM_P$=previous PCT matches for the entire user population
        $ET_{P1}$=exercise tracked most often by entire user population for submission $PTM_P$ FIG. 7 is a flow diagram illustrating the steps performed by a preferred embodiment of the exercise text match scoring algorithm 242 as part of the automatic exercise tracking method 240 shown in FIG. 2. FIG. 7 shows parsed and cleaned text (PCT) entering through the exercise text match algorithm 241 and into the exercise text match scoring algorithm 242. The parsed and cleaned text (PCT) first runs through the search string modifying algorithm 710 which creates modified PCT (MT). A exercise database fuzzy search on the modified PCT (MT) 720 is then run that generates exercise database fuzzy search results for exercises (e.g. walking, bench press, crunches, yoga, etc.) in relation to MT ($ESR_{(1 \ldots N)}$). The $ESR_{(1 \ldots N)}$ are analyzed at 722 to determine if each $ESR_{(1 \ldots N)}$ has the exercise time, distance and/or resistance quantity unit(s) (QU) for the applicable parsed and cleaned text (PCT) among all exercise time, distance and/or resistance quantity units associated with each $ESR_{(1 \ldots N)}$ (AQU). If a $ESR_{(1 \ldots N)}$ does not have QU that is a subset of AQU, then such $ESR_{(1 \ldots N)}$ is removed as a $ESR_{(1 \ldots N)}$. If a $ESR_{(1 \ldots N)}$ has QU that is a subset of AQU, then an entire user population data history lookup is run to find the lifetime total count for number of times each $ESR_{(1 \ldots N)}$ has been tracked by the system (EC) 730. A user data history lookup is also run to find each exercise denoted a "favorite exercise" (FE) for each $ESR_{(1 \ldots N)}$ 740 in relation to such user. If at 732 a $ESR_{(1 \ldots N)}$ is a FE, then the exercise tracking count score for each $ESR_{(1 \ldots N)}$ in relation to such user (ECS) is set equal to 50. If $ESR_{(1 \ldots N)}$ is not a FE, then at 734 if the lifetime total count for number of times each $ESR_{(1 \ldots N)}$ has been tracked by the system (EC) is less than 100, then ECS is set equal to −10. If $ESR_{(1 \ldots N)}$ is not a FE and EC is 100 or greater, then ECS=$(\log_{10}(EC)^4)/1000$. The exercise search score (ESS) for each $ESR_{(1 \ldots N)}$ is determined by the following formula: ESS=$\log_{10}(EDSR)*10$; where EDSR is the exercise database fuzzy search ranking number for each $ESR_{(1 \ldots N)}$. It is understood that the database fuzzy search ranking numbers are generated numbers with the largest number equating to the top match. Lastly, the algorithm determines the exercise text match scoring rank for each $ESR_{(1 \ldots N)}$ ($ER_{(1 \ldots N)}$). If at 736 the modified PCT (MT) contains more than one word, then $ER_{(1 \ldots N)}$=ECS+(ESS*100); otherwise, if MT contains only one word, then $ER_{(1 \ldots N)}$=(ECS*5)+ESS. The exercise to be tracked (E) is equal to $ER_1$ (e.g. the top ranked exercise), and such exercise to be tracked (E) is sent to the multi-exercise handling method 220.

The following is a description of an embodiment of the exercise text match scoring algorithm 242:
  i. Run PCT through the search string modifying algorithm to create MT.
     Run exercise database fuzzy search on MT for $ESR_{(1 \ldots N)}$;
     If QU is not a subset of AQU for each $ESR_{(1 \ldots N)}$, then such $ESR_{(1 \ldots N)}$ is removed as a $ESR_{(1 \ldots N)}$;
     Run entire user population data history lookup for EC for each $ESR_{(1 \ldots N)}$.
     Run user data history lookup for FE for each $ESR_{(1 \ldots N)}$ for such user.
     If $ESR_{(1 \ldots N)}$ is an FE, Then ECS=50;
     Else, If EC<100, Then ECS=−10;
     Else, ECS=$(\log_{10}(EC)^4)/1000$.
     ESS 32 $\log_{10}(EDSR)*10$.

Figure 8:
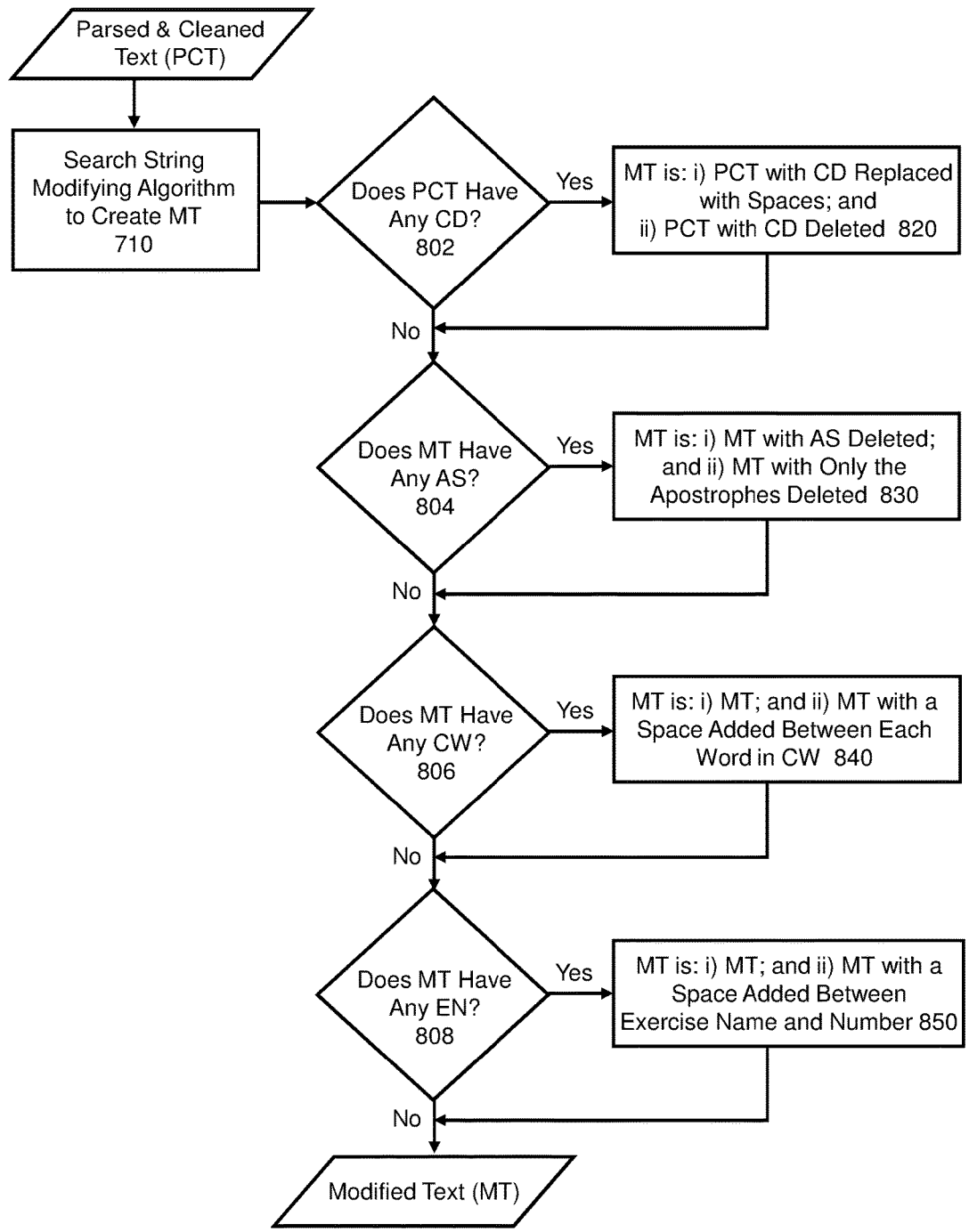
FIG. 8 is a flow diagram showing the steps performed by an embodiment of a search string modifying algorithm shown in FIG. 7.

If MT has multiple words, Then $ER_{(1 \ldots N)}$=ECS+ (ESS*100);
Else, $ER_{(1 \ldots N)}$=(ECS*5)+ESS.
$E=ER_1$.

ii. Definitions of terms:
   a. PCT=parsed text without exercise time, distance and/or resistance quantity numeric value(s) (QN) and exercise time, distance and/or resistance quantity unit(s) (QU) ($PT_{WNU}$) that has been cleaned by the exercise text cleaning algorithm
   b. MT=the modified PCT resulting from the search string modifying system
   c. $ESR_{(1 \ldots N)}$=exercise database fuzzy search results for exercises (e.g. walking, bench press, crunches, yoga, etc.) in relation to MT
   d. QU=exercise time, distance and/or resistance quantity unit
   e. AQU=all exercise time, distance and/or resistance quantity units associated with each exercise
   f. ECS=exercise tracking count score for each $ESR_{(1 \ldots N)}$
   g. EC=lifetime total count for number of times each $ESR_{(1 \ldots N)}$ has been tracked by system
   h. FE=exercise is a user denoted "favorite exercise"
   i. ESS=exercise search score
   j. EDSR=exercise database fuzzy search ranking number for each $ESR_{(1 \ldots N)}$
   k. $ER_{(1 \ldots N)}$=an exercise and its associated exercise text match scoring rank (e.g. $ER_1$ is the highest scoring exercise)
   l. E=an exercise (e.g. walking, bench press, crunches, yoga, etc.) to be tracked by system FIG. 8 is a flow diagram illustrating the steps performed by a preferred embodiment of the search string modifying algorithm 710 as part of the exercise text match scoring algorithm 242 shown in FIG. 7. FIG. 8 shows parsed and cleaned text (PCT) entering the algorithm, which may first determine at 802 if the PCT has any connecting dashes between words in PCT (CD). If PCT has connecting dashes between words in PCT (CD), then at 820 it may be determined that the modified PCT (MT) is: i) PCT with CD replaced with spaces, and ii) PCT with CD deleted. If PCT does not have any CD or PCT has run through the process at 820 in FIG. 8, then at 804 if MT has an apostrophe followed by an "s" ('s) (AS), then at 830 it may be determined that the MT is: i) MT with any AS deleted, and ii) MT with only the apostrophes deleted. If MT does not have any AS or MT has run through the process at 830 in FIG. 8, then at 806 if MT has multiple words connected with no space in between (CW), then at 840 it may be determined that MT is: i) MT, and ii) MT with a space added between each word in such CW. If MT does not have any CW or MT has run through the process at 840 in FIG. 8, then if MT has exercise name with a connected number (EN), then at 850 it may be determined that MT is: i) MT, and ii) MT with a space added between the exercise name and the number, irrespective of the order. If MT at 808 does not have any EN, or MT has run through the process 850 in FIG. 9, then MT is equal to MT.

The following is a description of an embodiment of the search string modifying algorithm 810:

i. If PCT has CD, Then MT is: i) PCT with CD replaced with spaces, and ii) PCT with CD deleted;
If MT has AS, Then MT is: i) MT with any AS deleted, and ii) MT with only the apostrophes deleted;
If MT has CW, Then MT is: i) MT, and ii) MT with a space added between each word in such CW;
If MT has EN, Then MT is: i) MT, and ii) MT with a space added between the exercise name and the number, irrespective of the order;
Else, MT=MT.

ii. Definitions of terms are:
   a. PCT=parsed text without exercise time, distance and/or resistance quantity numeric value(s) (QN) and exercise time, distance and/or resistance quantity unit(s) (QU) ($PT_{WNU}$) that has been cleaned by the exercise text cleaning algorithm
   b. CD=connecting dashes between words in PCT
   c. MT=the modified PCT resulting from the search string modifying system
   d. AS=an apostrophe followed by an "s" ('s)
   e. CW=multiple words connected with no space in between
   f. EN=exercise name with a connected number While the foregoing has been with reference to preferred embodiments, it will be appreciated that changes may be made from these embodiments without departing from the principles of the invention, the scope of which is defined by the appended claims.

The invention claimed is:

1. A computer-implemented method of automatic exercise tracking, comprising:
   receiving text from a user that describes an exercise that is to be tracked;
   parsing the received text into text segments;
   identifying automatically in each parsed text segment an exercise quantity value and an exercise quantity unit for said exercise that is to be tracked, said identifying comprising searching said parsed text segment for a quantity value followed directly by a quantity unit, and assigning said quantity value and said quantity unit to be said exercise quantity value and said exercise quantity unit for the exercise to be tracked, and upon not finding a quantity value followed directly by a quantity unit, selecting as said exercise quantity value and said exercise quantity unit a most frequently occurring quantity value and quantity unit for said exercise to be tracked;
   cleaning the parsed text segments to identify and remove words, connected spaces, and punctuation that are not used to identify exercise to produce parsed cleaned text;
   processing the parsed cleaned text segments using a text match algorithm to find said exercise that is to be tracked in each parsed cleaned text segment, comprising ranking each exercise text match found using a ranking process, and selecting the ranked exercise with a predetermined rank to be the exercise that is to be tracked; and
   reporting exercise tracking information for said exercise to be tracked.

2. The method of claim 1, wherein said parsing further comprises removing all quantity values and quantity units from said parsed text segments, and wherein said ranking said found exercise text matches comprises searching a past history of said user for previous matches, and selecting from said past history a most recent exercise tracked as said exercise to be tracked.

3. The method of claim 2, wherein upon an exercise match not being found in said searching, then searching a user population history for previous matches, and selecting an exercise that has been most often tracked as said exercise to be tracked.

4. The method of claim 3, wherein upon an exercise match not being found in said user population history, processing said parsed text using a search string modifying algorithm to create a modified text string; performing a fuzzy search on an exercise database for exercise results relevant to said modified text string; scoring said exercise results to create an exercise text match score; and selecting as said exercise to be tracked an exercise having the top score.

5. The method of claim 4, wherein said scoring comprises determining from a user data history lookup for said user whether an exercise of said exercise results is designated as a favorite exercise of said user, and, if so, scoring that exercise to have the highest score, otherwise, upon no favorite exercise designation being found, determining from an entire user population history a total count for a number of times each exercise has been tracked, and scoring the exercise with the highest count as the exercise with the highest score.

6. The method of claim 4, wherein said search string modifying algorithm creates said modified search string by performing one or more of: (i) removing, or replacing with spaces, connecting dashes between words, if any, (ii) removing an apostrophe followed by a letter "s" and removing an apostrophe only, if any, and (iii) inserting a space between connected words and numbers that have no space, if any.

7. The method of claim 1, wherein said searching for an exercise quantity value and an exercise quantity unit comprises performing a fuzzy logic search of said parsed text for a textual number or a numeric value, and upon finding said textual number or numeric value, performing a further fuzzy logic search of said parsed text for a match of a quantity unit term directly following said textual number or numeric quantity and, if found, assigning said textual number or numeric quantity to said exercise quantity value and assigning said quantity unit term to said exercise quantity unit.

8. The method of claim 7, wherein upon not finding said match of a quantity unit term, applying numeric value sequence pattern recognition logic rules that identify a sequence of numeric values associated with an exercise type, and if such logic rules are met assigning quantity unit terms to said exercise quantity units and assigning such exercise quantity units to the applicable numeric values.

9. The method of claim 7, wherein upon not finding said written number or numeric quantity, performing a further fuzzy logic search of said parsed text for a match of a quantity unit term, and, if found, assigning said quantity unit term to said exercise quantity unit, and, if not found, searching a user data history for said user for a most recently tracked exercise quantity unit for said exercise to be tracked, and setting the exercise quantity unit for said exercise to be tracked to be the most recently tracked exercise quantity unit.

10. The method of claim 9, wherein upon not finding a most recently tracked exercise quantity unit in said user data history, searching an entire user population history for a most frequently tracked exercise quantity unit for said exercise to be tracked, and setting said exercise quantity unit for the exercise to be tracked to be said most frequently tracked exercise quantity unit.

11. Non-transitory computer readable media embodying executable instructions for controlling a computer for an automatic exercise tracking method, comprising:
receiving text from a user that describes an exercise that is to be tracked;
parsing the received text into text segments;
identifying automatically in each parsed text segment an exercise quantity value and an exercise quantity unit for said exercise that is to be tracked, said identifying comprising searching said parsed text segment for a quantity value followed directly by a quantity unit, and assigning said quantity value and said quantity unit to be said exercise quantity value and said exercise quantity unit for the exercise to be tracked, and upon not finding a quantity value followed directly by a quantity unit, selecting as said exercise quantity value and said exercise quantity unit a most frequently occurring quantity value and quantity unit for said exercise to be tracked;
cleaning the parsed text segments to identify and remove words, connected spaces, and punctuation that are not used to identify exercise and produce parsed cleaned text;
processing the parsed cleaned text segments using a text match algorithm to find said exercise that is to be tracked in each parsed cleaned text segment, comprising ranking each exercise text match found using a ranking process, and selecting the ranked exercise with a predetermined rank to be the exercise that is to be tracked; and
reporting exercise tracking information for said exercise to be tracked.

12. The non-transitory computer readable media of claim 11, wherein said parsing further comprises removing all quantity values and quantity units from said parsed text segments, and wherein said ranking said found exercise text matches comprises searching a past history of said user for previous matches, and selecting from said past history a most recent exercise tracked as said exercise to be tracked.

13. The non-transitory computer readable media of claim 12, wherein upon an exercise match not being found in said searching, then searching a user population history for previous matches, and selecting an exercise that has been most often tracked as said exercise to be tracked.

14. The non-transitory computer readable media of claim 13, wherein upon an exercise match not being found in said user population history, processing said parsed cleaned text using a search string modifying algorithm to create a modified text string; performing a fuzzy search on an exercise database for exercise results relevant to said modified text string; scoring said exercise results to create an exercise text match score; and selecting as said exercise to be tracked an exercise having the top score.

15. The non-transitory computer readable media of claim 14, wherein said scoring comprises determining from a user data history lookup for said user whether an exercise of said exercise results is designated as a favorite exercise of said user, and, if so, scoring that exercise to have the highest score, otherwise, upon no favorite exercise designation being found, determining from an entire user population history a total count for a number of times each exercise has been tracked, and scoring the exercise with the highest count as the exercise with the highest score.

16. The non-transitory computer readable media of claim 14, wherein said search string modifying algorithm creates said modified search string by performing one or more of: (i) removing, or replacing with spaces, connecting dashes between words, if any, (ii) removing an apostrophe followed by a letter "s" and removing an apostrophe only, if any, and (iii) inserting a space between connected words and numbers that have no space, if any.

17. The non-transitory computer readable media of claim 11, wherein said searching for an exercise quantity value and an exercise quantity unit comprises performing a fuzzy logic search of said parsed text for a textual number or a numeric value, and upon finding said textual number or numeric value, performing a further fuzzy logic search of said parsed text for a match of a quantity unit term directly following said textual number or numeric quantity and, if found, assigning said textual number or numeric quantity to said exercise quantity value and assigning said quantity unit term to said exercise quantity unit.

18. The non-transitory computer readable media of claim 17, wherein upon not finding said match of a quantity unit term, applying numeric value sequence pattern recognition logic rules that identify a sequence of numeric values associated with an exercise type, and if such logic rules are met assigning quantity unit terms to said exercise quantity units and assigning such exercise quantity units to the applicable numeric values.

19. The non-transitory computer readable media of claim 17, wherein upon not finding said written number or numeric quantity, performing a further fuzzy logic search of said parsed text for a match of a quantity unit term, and, if found, assigning said quantity unit term to said exercise quantity unit, and, if not found, searching a user data history for said user for a most recently tracked exercise quantity unit for said exercise to be tracked, and setting the exercise quantity unit for said exercise to be tracked to be the most recently tracked exercise quantity unit.

20. The non-transitory computer readable media of claim 19, wherein upon not finding a most recently tracked exercise quantity unit in said user data history, searching an entire user population history for a most frequently tracked exercise quantity unit for said exercise to be tracked, and setting said exercise quantity unit for the exercise to be tracked to be said most frequently tracked exercise quantity unit.

* * * * *